US008697006B2

(12) United States Patent
Häivä et al.

(10) Patent No.: US 8,697,006 B2
(45) Date of Patent: Apr. 15, 2014

(54) APPLICATION OF A REAGENT TO A MATRIX MATERIAL

(75) Inventors: Veli-Mies Häivä, Espoo (FI); Anna Kaisa Kylmä, Luoma (FI); Juhani Luotola, Espoo (FI)

(73) Assignee: Orion Diagnostica Oy, Espoo (FI)

( * ) Notice: Subject to any disclaimer, the term of this patent is extended or adjusted under 35 U.S.C. 154(b) by 615 days.

(21) Appl. No.: 11/920,578

(22) PCT Filed: May 15, 2006

(86) PCT No.: PCT/EP2006/004536
§ 371 (c)(1), (2), (4) Date: Feb. 24, 2009

(87) PCT Pub. No.: WO2006/122733
PCT Pub. Date: Nov. 23, 2006

(65) Prior Publication Data
US 2009/0215193 A1 Aug. 27, 2009

(30) Foreign Application Priority Data
May 20, 2005 (GB) .................................. 0510337.9

(51) Int. Cl.
*G01N 33/52* (2006.01)

(52) U.S. Cl.
USPC ........... 422/419; 422/402; 422/421; 422/422; 422/423; 422/424

(58) Field of Classification Search
USPC ............. 435/7.2; 422/50, 400, 401, 402, 407, 422/408, 412, 418, 419, 420, 421, 422, 423, 422/424, 430
See application file for complete search history.

(56) References Cited

U.S. PATENT DOCUMENTS 3,511,740 A 5/1970 Sanders
3,722,696 A * 3/1973 Dwyer et al. ................. 210/435
3,992,158 A 11/1976 Przybylowicz et al.
4,046,513 A 9/1977 Johnson
4,181,500 A 1/1980 Cowsar et al.
(Continued)

FOREIGN PATENT DOCUMENTS

AU 1466383 A 3/1984
AU 8120787 A 5/1988
(Continued)

OTHER PUBLICATIONS

Columbus, Richard L. et al. "'Architextured' fluid management of biological fluids." Clinical Chemistry (1987) 33 p. 1531-1537.*
(Continued)

*Primary Examiner* — Christopher A Hixson
(74) *Attorney, Agent, or Firm* — Harness, Dickey & Pierce, P.L.C.

(57) ABSTRACT

A reagent or particles having reagent supported thereon are applied to a matrix material by a contact printing process for example in which the matrix material is brought into contact with a rotating contact roll having the reagent or particles having reagent supported thereon disposed thereon so as to transfer the reagent or particles having reagent supported thereon to the matrix material. Such a contact printing processes allow high speed and high volume production of an assay device.

66 Claims, 2 Drawing Sheets

(56) References Cited

U.S. PATENT DOCUMENTS

| | | | | |
|---|---|---|---|---|
| 4,256,693 | A | 3/1981 | Kondo et al. | |
| 4,278,763 | A | 7/1981 | Berger et al. | |
| 4,299,917 | A | 11/1981 | Berger et al. | |
| 4,647,430 | A | 3/1987 | Zweig | |
| 4,657,855 | A | 4/1987 | Corey et al. | |
| 4,689,240 | A | 8/1987 | Zweig | |
| 4,877,745 | A | 10/1989 | Hayes et al. | |
| 5,049,358 | A | 9/1991 | Lau | |
| 5,149,622 | A | 9/1992 | Brown et al. | |
| 5,252,496 | A | 10/1993 | Kang et al. | |
| 5,658,802 | A | 8/1997 | Hayes et al. | |
| 5,726,062 | A | 3/1998 | Numa et al. | |
| 5,763,262 | A | 6/1998 | Wong et al. | |
| 5,788,942 | A | 8/1998 | Kitani et al. | |
| 5,814,522 | A | 9/1998 | Zimmer et al. | |
| 5,851,838 | A | 12/1998 | Vetter et al. | |
| 5,958,790 | A | 9/1999 | Cerny | |
| 5,976,881 | A | 11/1999 | Klingner | |
| 5,981,287 | A | 11/1999 | Sinclair et al. | |
| 6,378,386 | B1 | 4/2002 | Schroder et al. | |
| 6,397,690 | B1 | 6/2002 | Schroder et al. | |
| 6,455,001 | B1 * | 9/2002 | Knappe et al. | 422/56 |
| 6,649,025 | B2 | 11/2003 | Mills et al. | |
| 6,770,485 | B2 | 8/2004 | Knezevic et al. | |
| 7,172,801 | B2 | 2/2007 | Hoying et al. | |
| 2001/0023075 | A1 | 9/2001 | Wong et al. | |
| 2002/0064887 | A1 | 5/2002 | Shalon et al. | |
| 2002/0187561 | A1 | 12/2002 | Wong et al. | |
| 2004/0214339 | A1 | 10/2004 | Profitt et al. | |

FOREIGN PATENT DOCUMENTS

| | | | |
|---|---|---|---|
| AU | 8153787 | A | 5/1988 |
| AU | 1664092 | A | 10/1992 |
| AU | 1387699 | A | 5/1999 |
| AU | 2006246649 | | 11/2006 |
| CA | 2608920 | | 11/2006 |
| CN | 101213449 | A | 7/2008 |
| EP | 0130335 | | 1/1985 |
| EP | 0045476 | | 10/1985 |
| EP | 0267724 | | 5/1988 |
| EP | 0342771 | | 11/1989 |
| EP | 0655625 | | 5/1995 |
| EP | 0821235 | | 1/1998 |
| EP | 1107004 | | 6/2001 |
| EP | 1882185 | | 1/2008 |
| GB | 1601283 | | 10/1981 |
| GB | 2426334 | | 11/2006 |
| JP | 58-7332 | | 1/1983 |
| JP | 62-24144 | | 2/1987 |
| JP | 63278517 | | 11/1988 |
| JP | 3-131757 | | 6/1991 |
| JP | 9-15232 | | 1/1997 |
| JP | 10-78431 | | 3/1998 |
| JP | 2001-305143 | | 10/2001 |
| JP | 2008541107 | | 11/2008 |
| NO | 20075942 | | 12/2007 |
| RU | 40110 | | 8/2004 |
| RU | 2007147456 | | 6/2009 |
| WO | WO-9216659 | A1 | 10/1992 |
| WO | WO-9924822 | A1 | 5/1999 |
| WO | 02/084251 | | 10/2002 |
| WO | 2005/031351 | | 4/2005 |
| WO | WO 2006/122733 | | 11/2006 |

OTHER PUBLICATIONS

Abstract of El-Nahhal, Issa M. "Encapsulation of phenolphthalein pH-indicator into a sol-gel matrix." Journal of Dispersion Science and Technology (2001) 22 p. 583-590.*

The PCT International Preliminary Report on Patentability issued Nov. 23, 2007 in related International Application No. PCT/EP2006/004536 (Publication No. WO 2006/122733).

Examiner's First Report issued by IP Australia on Oct. 8, 2010 in related Australian Patent Application No. 2006246649 (Publication No. AU 2006246649).

Notice of Reasons for Rejection issued by the Japanese Patent Office on Mar. 17, 2011 in related Japanese Patent Application No. 2008-511604 (Publication No. JP 2008541107), translation provided by Japanese associate.

Notice of Reasons for Rejection issued by the Japanese Patent Office on Jul. 7, 2011 in related Japanese Patent Application No. 2008-511604 (Publication No. JP 2008541107), translation provided by Japanese associate.

Canadian Office Action regarding Application No. 2,608,920, dated Oct. 17, 2012.

Australian Office Action regarding Application No. 2006246649, dated Feb. 23, 2012.

Australian Office Action regarding Application No. 2012200241, dated Apr. 10, 2012.

Australian Office Action regarding Application No. 2006246649, dated Jul. 24, 2012.

Australian Office Action regarding Application No. 2006246649, dated Sep. 18, 2012.

Australian Office Action regarding Application No. 2006246649, dated Dec. 5, 2012.

Australian Office Action regarding Application No. 2006246649, mailed Feb. 18, 2013.

Great British Search Report regarding Application No. GB0510337.9, dated Sep. 28, 2005.

International Search Report regarding Application No. PCT/EP2006/004536, mailed Nov. 3, 2006.

* cited by examiner

APPLICATION OF A REAGENT TO A MATRIX MATERIAL

CROSS-REFERENCE TO RELATED APPLICATIONS

This application is a 371 National Stage of International application No. PCT/EP2006004536, filed May 15, 2006 and published in English as WO 2006/122733 A2 on Nov. 23, 2006. This application claims the benefit of GB 0510337.9, filed May 20, 2005. The disclosures of the above applications are incorporated herein by reference.

The present invention relates generally to matrix materials having reagents applied thereto for use as test devices. In one aspect it relates to the application of the reagents to the matrix materials. In another aspect it relates to the test devices themselves which incorporate a matrix materials carrying reagents. It has particular application to reagents and matrix materials used in an assay, especially to produce a self-contained assay device comprising a sampler including the matrix material and reagents, and optionally also an indicator of the test result.

For on-site testing of an analyte suspected to be present in a sample, it is important to minimise the number of steps, the number of test components and the amount of reagent handling. Many commercially available tests consists of a sampler and some kind of a transportation unit to transport the newly taken sample to the laboratory for closer analyses. However, this practice has many drawbacks since it puts demands on the sampler, transportation medium and the transportation unit itself. It is of utmost importance to acknowledge an inevitable delay in receiving an assay result from the laboratory.

In order to overcome these deficiencies different kinds of on-site testing have been developed. There are some known, self-contained assay devices which support a reagent which detects the analyte by reacting therewith. A positive result may be indicated, for example, by a visible change. In general, this type of assay device support the reagent on a matrix material to which the sample is subsequently added for testing.

Well-known examples of this type of assay device are pregnancy tests and tests to determine protein, proteolytic enzymes and leukocytes in urinary samples. Other specific examples are as follows.

Such tests, compositions and agents are disclosed for example in U.S. Pat. Nos. 4,278,763, 4,299,917 and 4,657,855. These inventions exploit filter paper successively impregnated with different reagents and then dried. In order to carry out the test, a device for collecting urine is needed. After collection of urine it is applied into the sample receiving site of the test device or a test strip is brought into contact with the urine.

U.S. Pat. No. 5,049,358 discloses a device and method of determining presence and concentration of protein, as albumin or Bence Jones protein, in a test sample.

US-2004/0214339 relates to methods and devices of detecting proteins in an aqueous test fluid, wherein the buffer maintains the pH of the assay.

U.S. Pat. Nos. 6,397,690 and 6,378,386 relate to procedure and tools for quantifying surface cleanliness. The procedure measures particulate surface contamination by determining reflectivity loss before and after wiping.

U.S. Pat. No. 6,770,485 relates to methods of detecting biological material, particularly assays, methods and kits for detecting biowarfare agents such as micro-organisms, biological toxin, and the like. Said patent discloses a method where the sample is first collected by a swab or pad or the like. When contacted with one or more reagents the presence of protein produces a detectable signal (e.g. colour). In addition to a test strip impregnated with a protein indicator the test strip may also include sugar and pH detectors. Separate test strips for these may also be provided.

U.S. Pat. No. 5,981,287 relates to a method for the determination of house dust, wherein the house dust is treated with a protein detector. The dust material in the filter element is coloured when the protein detector reagent is applied to the filter.

In general, the matrix material may take a range of forms but is generally an absorbent material, one example being a paper web. Conventional products made from paper webs include several important properties. Usually they are used for cleaning or wiping and should therefore be highly absorbent and have good stretch characteristics. For example, U.S. Pat. No. 6,649,025 describes a wiping product made of separate plies that has different surface characteristics on each side of the product. The first and second outer ply can be laminated to each other. They can be embossed and nested together. The product disclosed in this patent is intended and especially suitable for cleaning and polishing any surface or object.

In general terms, performance of an assay can be achieved by using a compact assay device that contains all the necessary reagents and functions needed for the assay. In many assays two or more reagents may be used that are combined just prior to, during or after sampling. To fulfill these needs other technical solutions as compartmentalised structures with separate reagent reservoirs have been introduced. Several sample assay devices have been developed for various types of analysis that are aimed for facilitated sampling in both laboratory and non-laboratory environments. For non-laboratory environment it is also convenient to have non-liquid reagents that ascertain easy transport and waste disposal.

It is common in such assay devices that the reagents are applied to the matrix material, typically impregnated into an absorbent matrix material. This results in a ready to use test. A number of techniques for applying the reagent are known. However, many such known techniques are time consuming and expensive. It is common that known techniques are susceptible to mistakes. Some examples of known techniques are as follows.

A type of technique disclosed in U.S. Pat. No. 4,046,513 and GB-1,601,283, both dating from the late-1970s is to apply reagents to a matrix material using a stamping printing technique, for example silk-screen printing or offset printing in which a contact member having reagent disposed thereon is stamped onto the matrix material. More recently developed techniques are as follows.

EP-0,342,771 (as well as the related cases U.S. Pat. No. 5,763,262, US-2001/0023075 and US-2002/0187561) provides spray delivering method where the reagent is applied on to the matrix in a thin fluid stream through a small bore nozzle by using a commercial printing device. The method utilises also sound vibration and an electric field to control the application of reagent.

U.S. Pat. No. 5,958,790 discloses a method to impregnate reagents into nitro-cellulose paper by incubating papers in solution containing the reagent. This is very time consuming.

U.S. Pat. No. 5,252,496 utilises a line-spraying method to apply antibody to a membrane. Moreover, U.S. Pat. No. 5,149,622 discloses both a dropwise addition of reagent onto a filter, and alternatively, the use of areas of various patterns either sprayed or otherwise dispensed into the material of the matrix.

EP-1,107,004 discloses the application of a reagent to a hydrophilic target area of a non-absorbent substrate using a non-impact printing technique in which a stream of micro-droplets are directed at the substrate.

U.S. Pat. No. 5,658,802 discloses a technique for applying reagents onto a solid substrate to form a diagnostic array in which an array of drops of reagent is located in a pattern using ink-jet printing technology.

US-2002/0,064,887 discloses a printing system including a reservoir, capillary and nozzle for depositing liquids on a solid substrate.

In overview, the techniques used to apply reagents to the matrix material have become more and more sophisticated and technically complex. Clearly this puts demands on the technical approach. The first aspect of the invention is concerned with improving the technique for applying reagents to a matrix material.

According to a first aspect of the present invention, there is provided a method of applying a reagent or particles having reagent supported thereon to a matrix material, the method comprising printing the reagent or particles onto the matrix material by bringing a contact roll having disposed thereon the reagent or the particles having reagent supported thereon into contact with the matrix material while the contact roll is rotated and the contact roll and the matrix material are relatively moved. Further according to the first aspect of the invention, there is provided a matrix material having reagents or particles applied by this method.

It has been appreciated that by exploiting such a contact printing technique, there is achieved a cheap, fast and production-friendly way of manufacturing large quantities in a short period of time. For example, the hereinafter described embodiment exploits a roll-to-roll printing technique and apparatus which are standard in the field of printing in general. Such standard roll-to-roll printing techniques enable high-speed, high-volume production with a uniform quality.

The method performed is clearly distinct from the techniques performed by hand or utilising sophisticated spraying or ink jet type of approaches. The method used in the present invention is more robust than such known techniques and is therefore applicable to large scale continuous-flow production. Similarly, the method is not as susceptible to quality variation as the known techniques.

The matrix material with reagent applied thereto is particularly useful in a self-contained assay device suitable for clinical or hygiene on-site testing since it is ready to use containing necessary reagents for the assay. For example the assay device may comprise a sampler and indicator of test result. The utility value is also high since no device is needed for reading the test result.

The use of such a printing technique also has the advantage of facilitating application of reagent or particles to the matrix material in a predetermined pattern. For example the predetermined pattern may be chosen to increase sample concentration at the site of the reagents or particles, or may be one or more alphanumeric symbols which can assist the user. This may be achieved by the reagent or particles being initially disposed on the contact member in the pattern.

The method is applicable for printing reagents in liquid form, for example in solution, but is equally applicable for printing reagents which are supported on particles. A useful application is in a chromatographic assay. Furthermore, the method is similarly applicable to printing particles which do not support any reagent.

The reagent may be of any type including a single compound or a mixture. The invention is particularly applicable to a reagent capable of acting as an assay for at least one chemical or biological analyte in a sample or capable of detecting the pH of a sample. One advantageous reagent is a ligand or an anti-ligand. Some further specific examples of useful reagents are given below.

The matrix material may be of any type which is capable of supporting the reagent or particles, including but not exclusively matrices, paper, a membrane or a dip slide. Often the matrix material is absorbent so that the reagent or particles impregnate the matrix material which facilitates retention of the reagent or particles. Similarly use of an absorbent material can facilitate addition of a sample for reaction with the reagent or particles. Thus, the invention is particularly applicable to a matrix material for use in an assay device, particularly an assay device suitable for on-site testing. In such a device, the matrix material may also be enclosed in a mounting forming an assay casing or cartridge.

The absorbent capacity of the matrix material may be chosen by the selection of the matrix material. The matrix material may be for example but without limitation woven or non-woven cellulose, viscose, polypropylene, polyester, polyamide, or a blended mixture of those. The matrix material may have a surface structure or it may be creped to increase the surface wicking properties of the absorbent material. The thickness of the matrix material may also be adjusted to achieve the desired absorbent capacity.

Advantageously, there may be at least one layer of further material laminated with the matrix material. The laminating material may have a variety of different purposes, some examples of which are as follows. Different laminating procedures may also be used to improve both sample detaching and concentration on the matrix. The further material may be an impermeable layer on one or both sides of the matrix material. The further material may give additional rigidity to the device. The further material may be a semi-permeable material layer, for example to reduce or prevent either leaching or leaking of reagents from the matrix material during sampling.

The second aspect of the present invention is concerned with improving the operation of a test device incorporating a matrix material supporting a reagent.

According to the second aspect of the invention there is firstly provided a test device comprising:

two impermeable layers; and a layer of matrix material arranged between the impermeable layers, the matrix material carrying a reagent, and one of the impermeable layers having a plurality of openings aligned with the matrix material and through which a sample may be applied to the matrix material.

For performance of a test or assay, a sample may be applied to the matrix material, and hence to the reagent carried on the matrix material, through the openings. Particular advantages are achieved by the provision of a plurality of openings as compared to say a single large opening, as follows.

The provision of plurality of openings is observed to have the result of increasing the intensity of the reaction with the reagent and hence improving the test results, for example making a colour change more visible. The reason for achieving this is not fully understood but is believed to be achieved due to capillary action inside the matrix material, as follows. The openings may be viewed as a providing for performance of a separate reactions under each opening, in that the sample comes into contact with the matrix material under each opening. This results in a local saturation of the matrix material by the sample at each location under an opening and the sample diffuses outwardly towards the periphery of each opening. It is believed that this causes a concentration barrier which results locally in a more intense reaction.

The plurality of openings can also assist in extracting a sample from a surface by means of the edges of each of the openings formed in the impermeable layer scraping the surface.

According to the second aspect of the invention there is secondly provided a test device comprising:

two impermeable layers;

a layer of matrix material arranged between the impermeable layers, one of the impermeable layers having at least one opening aligned with the matrix material and through which a sample may be applied to the matrix material; and a semi-permeable layer extending across the at least one opening, the semi-permeable layer being made of a semi-permeable material which is capable of allowing a sample to pass therethrough whilst limiting backflow of the reagent.

The semi-permeable layer has the advantage of reducing the leaching or leakage of reagents from the matrix material during sampling. Moreover it reduces the leaching or leakage of moisture back to the sampled surface.

To allow better understanding, an embodiment of the present invention will now be described by way of non-limitative example with reference to the accompanying drawings. In the drawings.

There is first described an apparatus which is operable to perform a contact printing technique suitable for applying reagents to a matrix material by printing. More precisely the apparatus impregnates reagents into a matrix comprising a high speed, high volume standard roll-to-roll printing technique usually employed for printing of documents rather than manufacturing of diagnostic tests. The roll-to-roll technique is in itself known but will be described to the extent that is necessary to exploit the invention.

The apparatus is designed to apply bromocresol green (BCG) reagent comprising bromocresol green, acetic acid, methyl acetate and alcohol to the matrix material. Despite this, it is to be noted that the technique is not limited to BCG, but in general any reagents can be applied the matrix using a similar technique. The technique is equally applicable for applying particles which support a reagent. Support of the reagent on particles is of particular application to a reagent which is a ligand or an anti-ligand. The particles may be of any kind, material or size, for example latex particles, colloidal gold particles or magnetic particles. The particles may be either coloured or not coloured.

In this embodiment the matrix material 1 is a paper web, but it is to be noted that the matrix material can take any form, preferably being absorbent to facilitate its use in an assay device.

Roll-to-roll fabrication of the bromocresol green chemistry based protein test can be divided in three separate stages, namely: 1) pre-treatment of matrix material, 2) printing of the reagent solution onto the test matrix, and 3) lamination of the printed test matrix with one or more auxiliary layers, to form a test entity with one or more layers in a compact form. The apparatus for performing these three stages will now be described but it is to be noted that the stages do not need to be performed in a given order.

Pre-treatment of the matrix material 1 can be performed either by washing the matrix material 1 in an acid bath or by printing the required acid solution directly onto the matrix material. The acid can be any kind of acid (eg citric acid, acetic acid, ascorbic acid, tartaric acid) and its function is to buffer the test matrix against small pH changes. Accordingly, it increases the reliability and the stability of the test. Pre-treatment by a washing process includes immersion of the matrix material 1 into an acid bath containing acid of predetermined pH, until the matrix material 1 is thoroughly wetted, followed by a subsequent drying period. Pre-treatment by printing can be either a roll-to-roll process or stop-and-go type of process.

Figure 1:
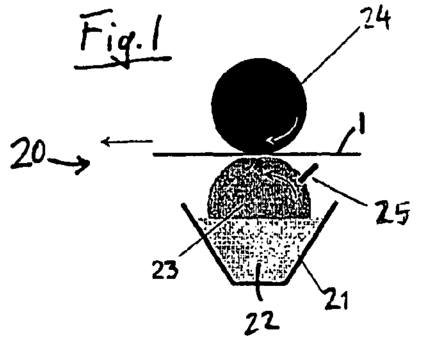
FIG. 1 is an illustration of a pre-treatment process apparatus.

FIG. 1 is an illustration of a pre-treatment process apparatus 20 employing roll-to-roll gravure-printing as a printing technique for applying the pre-treatment and using citric acid as a pre-treatment reagent. In FIG. 1, and in the subsequent figures, arrows indicate the flow direction of the matrix material 1. The pre-treatment process apparatus 20 is arranged as follows.

An open tray 21 contains the pre-treatment acid 22. A contact roll 23 is partly submerged in the acid 22 so that the acid 22 is deposited on the contact roll 23 as it rotates. The contact roll 23 contacts the matrix material 1 against a pressure roll 24 disposed on the opposite side of the matrix material 1 and also in contact with the matrix material 1. A wiper 25 is arranged against the contact roll 23 to remove excess acid 22 prior to contact with the matrix material 1 as the contact roll 23 rotates.

In operation, the contact roll 23 and pressure roll 24 are rotated at the same speed whilst the matrix material 1 is fed therebetween so that it moves relative to the contact roll 23 and pressure roll 24. The contact roll 23 transfers acid 22 from the tray 21 to the matrix material 1 and, by virtue of the contact with the matrix material 1 under pressure from the pressure roll 24, prints the acid 22 onto the matrix material 1.

Figure 2:
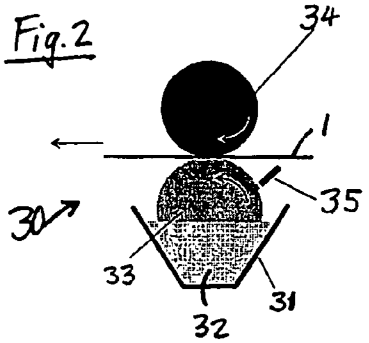
FIG. 2 is an illustration of a reagent printing process apparatus.

Application of the reagent 32, which is BCG in this example, is performed using the same conventional printing technique as described above for the pre-treatment stage. In particular, FIG. 2 is an illustration of the reagent printing process apparatus 30 employing roll-to-roll gravure-printing as a printing technique for applying the reagent 32. The reagent printing process apparatus 30 is arranged as follows.

An open tray 31 contains the reagent 32. The viscosity of the reagent 32 may range from 5 to 5000 cP, but preferably the viscosity is between 100-1000 cP. A contact roll 33 is partly submerged in the reagent 32 so that the reagent 32 is deposited on the contact roll 33 as it rotates. The contact roll 33 contacts the matrix material 1 against a pressure roll 34 disposed on the opposite side of the matrix material 1 and also in contact with the matrix material 1. A wiper 35 is arranged against the contact roll 33 to remove excess reagent 32 prior to contact with the matrix material 1 as the contact roll 33 rotates.

In operation, the contact roll 33 and pressure roll 34 are rotated at the same speed whilst the matrix material 1 is fed therebetween so that it moves relative to the contact roll 33 and pressure roll 34. The contact roll 33 transfers reagent 32 from the tray 31 to the matrix material 1 and, by virtue of the contact with the matrix material 1 under pressure from the pressure roll 34, prints the reagent 32 onto the matrix material 1.

In the case of the reagent printing process apparatus 30 and as distinct from the pre-treatment process apparatus 20, a gravure printing process is applied by means of the contact roll 33 having a recess in a predetermined pattern so that the reagent 32 is disposed on the contact roll 33 in that recess and is applied to the matrix material 1 in the predetermined pattern of the recess. Any predetermined pattern may be used as appropriate for the use of the reagent. One type of predetermined pattern is of one more alphanumeric characters, for example one or more letters, or symbols, or combinations thereof. These might for example indicate the result of an assay, for example by terms such as "clean", "dirty", "positive", "+" ("++", "+++" etc), "negative" or "−".

Figure 3:
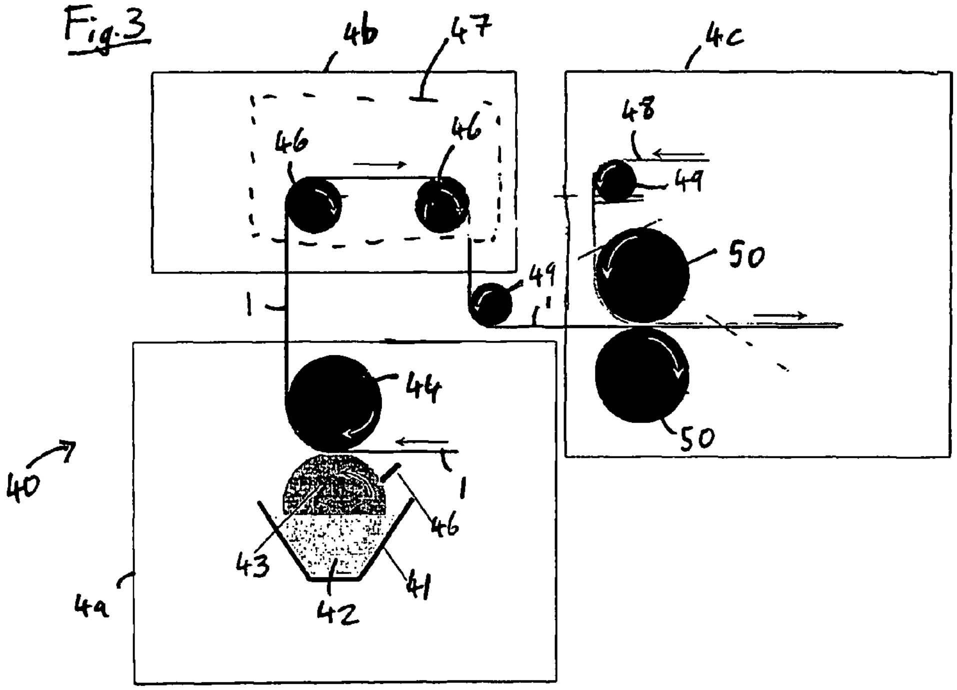
FIG. 3 is an illustration of a lamination process apparatus.

The matrix material 1 may be laminated with a further layer 48. In general, such lamination can be done either by using a roll-to-roll process or stop-and-go type of process, but the former is preferable. A suitable lamination process apparatus 40 is shown in FIG. 3 and arranged as follows.

In a first section 4*a* of the lamination process apparatus 40, glue 42 is applied to the matrix material 1 using the same conventional printing technique as described above for the pre-treatment stage and the reagent stage. In particular, the first section 4*a* employs roll-to-roll gravure-printing as a printing technique for applying glue 42 and is arranged as follows.

An open tray 41 contains the glue 42. A contact roll 43 is partly submerged in the glue 42 so that the glue 42 is deposited on the contact roll 43 as it rotates. The contact roll 43 contacts the matrix material 1 against a pressure roll 44 disposed on the opposite side of the matrix material 1 and also in contact with the matrix material 1. A wiper 45 is arranged against the contact roll 43 to remove excess glue 42 prior to contact with the matrix material 1 as the contact roll 43 rotates.

In operation, the contact roll 43 and pressure roll 44 are rotated at the same speed whilst the matrix material 1 is fed therebetween so that it moves relative to the contact roll 43 and pressure roll 44. The contact roll 43 transfers glue 42 from the tray 41 to the matrix material 41 and, by virtue of the contact with the matrix material 1 under pressure from the pressure roll 44, prints the glue 42 onto the matrix material 1.

In a second section 4*b* of the lamination process apparatus 40, the glue 42 on the matrix material 1 is dried. In the second section 4*b*, the matrix material is passed by a number of valve rolls 46 through a drier 47 which applies hot air to the glue 42 on the matrix material 1.

In a third section 4*c* of the lamination process apparatus 40, the further layer 48 is laminated with the matrix material 1 by adhering it using the glue 42. The matrix material 1 and the further layer 48 are fed using valve rolls 49 into contact with each other between a pair of pressure rolls 50. The pressure rolls 50 apply pressure to the matrix material 1 and the further layer 48 causing the glue 42 to adhere them together. The pressure rolls 50 are operated at room temperature to apply a pressure between for example 0.5 to 10 bar, preferably 2 to 4 bar.

The glue 42 may be a hot glue or a cold glue. If the glue 42 is a cold glue, it may be added onto a matrix material in a liquid form and dried in the second section 4*b* before the lamination of the further layer 48. Another useful type of cold glue which may be used is an ultraviolet (UV) curing glue. In this case, instead of the second section 4*b* for drying the glue 42, there may be employed a section which applies UV radiation to cure the glue 42. If the glue 42 is a hot glue, the glue 42 is a thermoplastic material and is added onto the matrix material 1 at a temperature above glass transition temperature. In this case drying in the second section 4*b* is unnecessary but both pressure and temperature are then used for adhering to the matrix material 1 and the further layer 48 together.

In the lamination process apparatus 40, the glue 42 is applied to the matrix material 1 but it could alternatively be applied to the further layer 48.

The lamination process apparatus 40 can be used to lamination more further layers if needed. The further layer 42 may take a number of different forms. Examples of possible further layers (which may be used in any combination) include:

a) plastic materials used as a stiffener and/or as a protective layer;

b) impermeable materials used as a pattern and/or as a protective layer;

c) semi-permeable materials used as a protective layer, and d) wicking membrane used as an additional sample absorbent layer.

The thicknesses of matrix material 1 and the further layer 48 used in the above described apparatuses 20, 30 and 40 are typically in the range from 1 μm to 500 μm, but preferably in the range from 1 μm to 100 μm.

In the apparatus described above, the matrix material 1 is fed at the same speed as the peripheral speed of the rolls, for example the contact roll 43 and the pressure roll 44. Also, each pair of opposed rolls, for example the contact roll 43 and the pressure roll 44 are of the same size. However, these features may be varied in different applications, for example exploiting rolls of different diameters and operated at speeds which differ from each other and/or from the speed of the matrix material 1.

Figure 4:
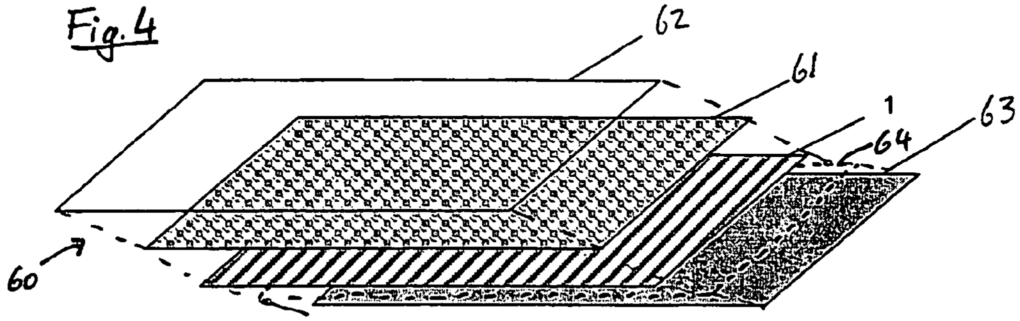
FIG. 4 is an exploded perspective view of a test device formed by the laminated matrix material.

A test device 60 is shown in FIG. 4 and will now be described. The test device 60 may be formed using the above described apparatuses 2, 3 and 4, the test device 60 being formed simply by cutting out a portion of the continuous matrix material 1 output from the lamination process apparatus 40.

The test device 60 comprises a layer of the matrix material 1 having the reagent applied thereto, laminated with three further layers, namely a semi-permeable layer 61 adjacent the matrix material 1; an impermeable surface layer 62 outside the semi-permeable layer 61; and an impermeable base layer 63 adjacent the matrix material 1 on the opposite side from the semi-permeable layer 61.

The semi-permeable layer 61 is optional and may in some embodiments of the test device 60 be omitted.

Optionally, the test device 60 may further comprise a wicking layer 64 between the matrix material 1 and the impermeable base layer 63 to enhance the absorption of the sample by the matrix material 1.

The impermeable surface layer 62 and the impermeable base layer 63 create a seal around the edge of the matrix material 1. The seal may be created intrinsically in the lamination process or may be created in a separate step.

The impermeable surface layer 62 and the impermeable base layer 63 prevent liquid from reaching the matrix material, except in a controlled manner as will now be described. To allow a sample to reach the matrix material 1, the impermeable surface layer 62 may be removable, or else may include openings so that it is not continuous, for example by being physically modified by removing a portion thereof.

Figure 5:
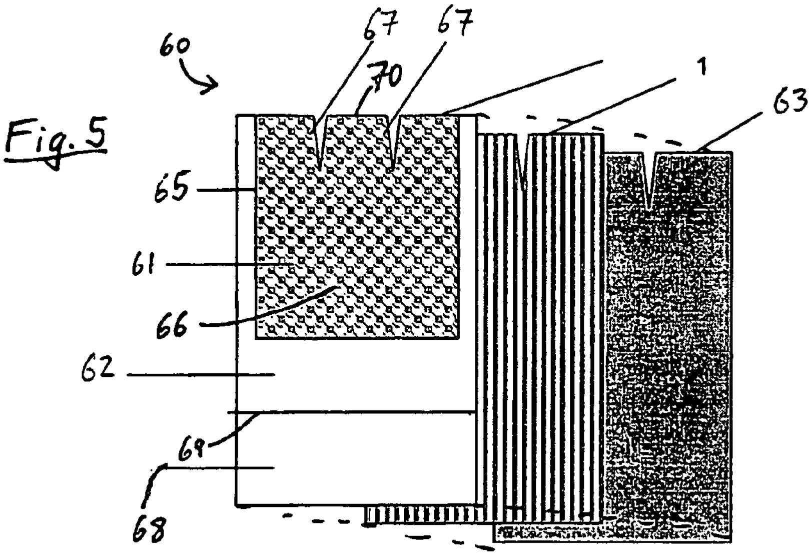
FIG. 5 is an exploded top view of one embodiment of the test device.
Figure 6:
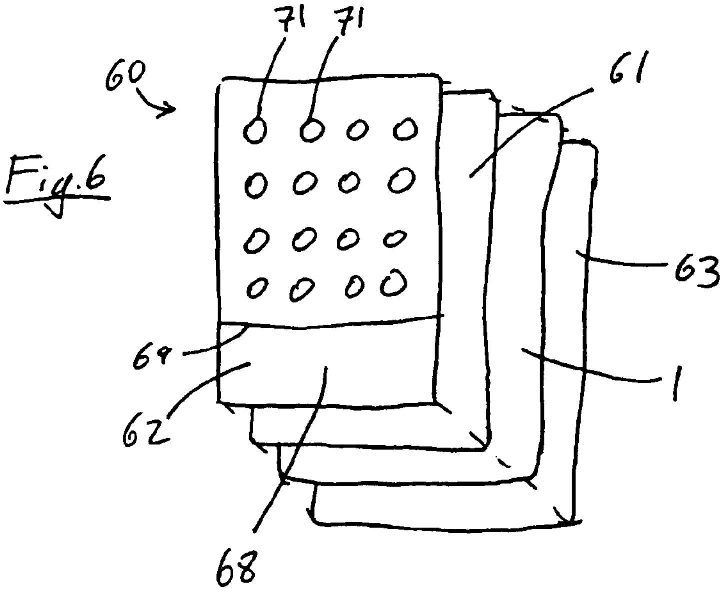
FIG. 6 is an exploded top view of another embodiment of the test device.

Two examples of the test device 60 in which the surface layer 62 includes openings are shown in FIGS. 5 and 6.

In the example of FIG. 5, the surface layer 62 has a single opening 65 formed at one end of the test device 60 exposing an area 66 of the semi-permeable membrane 61 which acts as a sampling surface for receiving a sample. In use the sample may be applied to the area 66 by wiping the test device over a surface, by dropping a fluid sample onto the test device 60 or by contacting the edge 70 of the test device adjacent the opening 65 against a solid sample or into a fluid sample. The surface layer 62 may initially be complete with the opening 65 being formed by removing a portion of the surface layer 62, for example by providing perforations in the surface layer around the edge of the opening 66.

In addition, the test device 6 is provided with two (or in general any number of) incisions 67 formed in the opening 65 and extending through the entire thickness of the test device 60 to allow sample collection from a sharp object such as a knife which is slid through an incision 67 by a user.

The size and shape of the incisions 67 and the opening 65 may be altered according to needs of the application. The opening 65 may as mentioned have any size or shape, for example a plain cut of the edge 70, an extension of the short cut or part thereof, a projection of the short cut, wherein the projection may have any size or shape. Naturally, said features may as well be on the long edge of the test device 60 instead of the short edge 70.

In the example of FIG. 6, the surface layer 62 has a plurality of openings 71. In this case there are sixteen openings 71 but this number can be varied. The openings 71 are circular but could have other shapes. The openings 71 are arranged in a regular array which although not essential does have the advantage of allowing the openings 71 to be packed together. The provision of the plurality of openings 71 in the example of FIG. 6 is observed to provide a more intense test result as compared the single opening 65 in the example of FIG. 5. This is believed to arise due to capillary action creating a local concentration boundary in the matrix material 1 under each opening 71 as described above. The plurality of openings 71 also assist in detachment of a sample from a surface as the edges of each opening 71 scrape the surface.

In both the examples of FIGS. 5 and 6, the remainder of the surface layer 62 outside the opening 65 or the openings 71 forms a grip 68 for a user. The grip 68 may be sectioned out from the opening 65 or the openings 71 by a fold 69. The degree of the angle of the fold 69 and the size and shape of the grip 68 may be altered according to requirements of the application.

Alternatively, a wicking channel may also be arranged as a projection of a plane with a small cut opening exposing the reagent matrix 1 in the cross sectional view of the test device 60.

There is a danger that reagents applied to the matrix material 1 are released during use, causing a regent flow from the matrix material 1 to a surface or object under examination. This flow may become evident when the surface is moistened for sampling in order to assist release of sample from the surface and consequently transfer the sample into the matrix material 1 of the sampler to react the reagent with an analyte in the sample. The wetted matrix material 1 may not be able to prevent the back flow due to high level of moisture incorporated during sampling.

Accordingly, a desirable one-way flow can be ascertained by different means.

One option is that the material of the semi-permeable layer 61 may be chosen to reduce or prevent the reagent from leaching from the matrix material 1. For example, the semi-permeable layer 61 may be made of a hydrophobic layer. A suitable hydrophobic material is a non-woven polypropylene material. The material may be either permanently or non-permanently hydrophobic or hydrophilic depending on the application. The materials used inhibit the flow of the reagent from the matrix material 1 after becoming moistened by the surface under examination. Similarly, it inhibits a back flow of the sample to said surface. From hygiene point of view this is a very important feature because it reduces or prevents the sample, which may contain micro-organisms, from re-contaminate the surface. Moreover, the surface remains dry also after sampling and does not become a platform for further contamination problems.

This effect is achieved by the semi-permeable layer 61 extending across the opening 65 or the openings 71. This results from the construction shown in FIG. 4 in which the semi-permeable layer 61 extends across the entire area of the matrix material 1 between the matrix material 1 and the surface layer 62. However other constructions in which the semi-permeable layer 61 extends across the opening 65 or the openings 71 are possible, for example with the semi-permeable layer 61 only extending over the area of the opening 65 or the openings 71 or being in front of the surface layer 62.

Another example of means to prevent a material from leaching out of the test device 60 is to use, for example as shown in FIG. 5, the impermeable surface layer 62 with an opening 65 providing a wicking surface, channel or any area for the moistened sample to enter the matrix material 1. The construction of the opening 65 may be a simple cut or a projection designed for reaching close quarters.

Optionally, either one or both of the impermeable surface layer 62 and the impermeable base layer 63 is transparent in the region adjacent opening 65 or the openings 71. This allows inspection of the matrix material 1 to determine the test result where this is a visible change.

The test device 60 may be designed to improve the concentration of the sample at the site where the reagent is applied to the matrix material 1. One option is to apply a relief to the matrix material 1, for example by a printing technique, which relief achieves this. Another option is to apply, for example by printing, an impermeable ink in a pattern which so improves the concentration. The pattern of the relief or impermeable ink may be any suitable pattern, the technique being known in other fields and used in wiper products used for cleaning. For example, the pattern of the relief or the impermeable ink may by an embossed array of grooves, grids or circles to reduce spreading of the liquid and/or to improve liquid flow and concentration into a small surface area.

To improve detachment of a sample from the sample surface, the test device 60 may include an appropriate laminated layer, for example an impermeable surface material selected to have a favourable surface structure for sample detachment. The patterns used for sample detaching may be embossed grooves, nodules or alike patterns, and may be part of the material pattern or may be embossed to said material during the test manufacturing process. The surface structure may also be used to concentrate the detached sample on the matrix material 1. The impermeable laminate may be perforated to form surface patterns, like those described for imprinted surface pattern, on the absorbent material layer.

Another option is that an impermeable material layer is used to give a desired degree of rigidity and form to the test device 60. This material can also form a housing for the matrix material 1. Accordingly, the matrix material 1 may be enclosed in a mounting (a casing or cartridge) which supports the matrix material 1 and creates conditions which enables longer storage times for the test. The housing may contain perforation for application of sample and a display for detection of analyte. The overall test device 60 may have desired shape and size depending on the sample and user requirements.

Another option is to use a blister package having a liquid compartment containing liquid or gel-like surface moistening agent. The compartment may be a separate item attached to the test device 60 by a separate assembly process. The moistening agent is released for example by pushing and breaking the blister package from one side.

It is also possible to apply, for example by printing using the printing technique used for the reagents, a conductive material to the matrix material 1. Such a conductive material may enable connection of the test device 60 to an outside current supply, for example to enable warming or heating of the test device 60. Such warming and heating of the test device 60 can be exploited with the BCA reagents to improve the sensitivity of the protein detection. The sensitivity of the BCA method is dependent on time and temperature. Accordingly, also test time can be used to improve the sensitivity. Warming and heating of the test device 60 up to +40-100° C., preferably 55° C. also enables detection of reducing sugars, which would not be detected at room temperature. Moreover, exploitation of a current enables an electrophoretic separation of compounds with different charge. Furthermore, it enables magnification of detection signal by electrical means. In the case of electrophoretic separation, it is possible to apply, for example using the printing technique used for the reagents, a gel to the matrix material 1.

Similarly, it is possible to apply, for example using the printing technique used for the reagents, a power source in the form of a thin film battery (sometimes called a paper battery) for low power applications, for example of the type manufactured by Enfucell Ltd and VoltaFlex Corporation.

In more sophisticated applications, a selective or non-selective microbial growth can be achieved by additionally applying a substrate or culture medium to the matrix material 1 or other component of the test device 60, for example using the printing technique used for the reagents. The culture medium may be selective or non-selective and may be in dry or ready-to-use format. The culture medium may be used in combination with a conductive material or thin film battery arranged to provide heating or warming of the sample to a suitable temperature, typically being in the range from 30° C. to 45° C., preferably 37° C. This may be done, for example, by passing current through a resistance wire or passing a current between two electrodes on the matrix material 1.

For even more specific analysis, the reagent applied to the matrix material 1 may be any ligand or anti-ligand can be impregnated into/onto the matrix to enable detection of chosen biological markers.

In many test devices, the reagent has a reaction which produces a visible change. In such a case the outer surface of the test device 60 may be printed with a reference panel indicating the meaning of different changes in the matrix material. For example the reference panel may correlate different colours with different reaction intensities and hence calibrate the test to some extent.

The above described features of the test device 60 may be applied individually or in any combination. Indeed they may also be applied to a test device in which the reagent is applied to the matrix material by some other technique than contact printing.

As already mentioned, the reagent may take any form. Merely by way of example and without limitation to the scope of the invention, some specific test procedures with corresponding reagents will now be described. Unless indicated otherwise, the methods used are standard chemistry, biochemistry and physical techniques.

Similarly the sample may take any form. The sample may be a liquid. In other cases, the sample may be a substance other than a liquid, for example a biological sample such as a protein. In this case, the sample may be moistened or wetted by a liquid, for example by water or a buffer solution, to assist transfer to the matrix material 1. In this case the semi-permeable membrane 61 allows the sample to pass therethrough in suspension or solution.

A protein test procedure may be applied as follows. This procedure exploits a reagent composition with ability to react with low concentrations of protein. The reagent composition may utilise any of the known protein detection methods including but not limited to bromocresol green (BCG), pyrogallol red, Coomassie blue, bicinchoninic acid (BCA)-copper-complex. The interaction between the reagent and the protein produce either a visually or instrumentally detectable and/or a measurable result. According to the procedure, a moistened surface is wiped with the test device 60. Moistening may be achieved by exploiting a separate device for addition of moistening agent to the sample surface, or by a compartment containing a pre-determined amount of moistening agent attached to the test device 60 to be opened and released to moist the surface to be sampled. The pressure used against the surface during sampling forces the moisture comprising the sample through the semi-permeable layer 61. The excess moisture left at the sample surface may be absorbed into the matrix material 1 through the opening 65 exposing a wicking channel as described above. The same wicking channel may also be used for taking a sample from a liquid. If the sample contains protein it will react with the reagent provided in the matrix material 1. This will cause the reagent to change its colour from yellow-orange to green which, accordingly will be visually detectable through the transparent semi-permeable layer 61 either qualitatively or quantitatively.

A pH test procedure may be applied as follows. A BCG reagent as described above may also be used as a pH indicator simply by adjusting the pre-treatment acid 22 applied to the matrix material 1 to neutral pH range, or by choosing a reagent matrix material with neutral pH. The pH indicator property of the BCG reagent may be exploited as an independent pH test or as a simultaneous measurement of both protein and pH by partition the sample contact area into pH- and protein measurement area.

The test device 60 may be supplied as part of a diagnostic kit. Such a kit is suitable for use in the present methods and is in general useful for diagnosis and assessment of protein in samples taken from surfaces for hygiene monitoring. The contents of the kit will be suitable for the assay format that the kit is intended for. Typically the kit comprises a test device 60 as described above or a non-laminated matrix material 1 containing reagents for detection of e.g. protein, carbohydrate, sugar, pH, ligand or anti-ligand, the presence of which are indicated by colour or precipitate production. In general a kit may comprise other reagents or components for use in the particular assay, such as buffers, precipitators, labelling and/or detection means. In one embodiment, the kit may include instruction means, such as package insert instructing the user of the kit as to the kit contents and assay format.

The invention claimed is:

1. A test device for wiping over a surface to extract a sample, the test device comprising:

two impermeable layers;

a layer of absorbent matrix material arranged between the impermeable layers and located immediately adjacent both impermeable layers, the matrix material carrying a reagent and having a patterned surface, and one of the impermeable layers having a plurality of openings aligned with the matrix material and through which the sample may be absorbed into the matrix material as facilitated by the wiping over the surface, wherein the patterned surface of the matrix material reduces spreading and increases a concentration of the sample in regions of the matrix material corresponding to the plurality of openings.

2. The test device according to claim 1, further comprising a semi-permeable layer disposed between the absorbent matrix material and one of the impermeable layers which extends across the plurality of openings, the semi-permeable layer being made of a semi-permeable material which is capable of allowing the sample to pass therethrough whilst limiting backflow of the reagent.

3. The test device according to claim 2, wherein the semi-permeable material is hydrophobic.

4. The test device according to claim 2, wherein the semi-permeable material is non-woven polypropylene.

5. The test device according to claim 2, wherein the semi-permeable layer is arranged between the layer of matrix material and the one of the impermeable layers having the plurality of openings.

6. A test device for wiping over a surface to extract a sample, the test device comprising:

two impermeable layers;

a layer of absorbent matrix material arranged between the impermeable layers and located immediately adjacent a first of the two impermeable layers, the matrix material having a reagent applied thereto, one of the impermeable layers having at least one opening aligned with the matrix material and through which the sample may be absorbed into the matrix material as facilitated by the wiping over the surface; and a one-way flow semi-permeable layer extending across the at least one opening and located immediately adjacent the absorbent matrix material and a second of the two impermeable layers, the one-way flow semi-permeable layer being made of a semi-permeable material which only allows the sample to pass in a direction towards the matrix material, but limits backflow of the reagent from the matrix material.

7. The test device according to claim 6, wherein the semi-permeable material is hydrophobic.

8. The test device according to claim 6, wherein the semi-permeable material is non-woven polypropylene.

9. The test device according to claim 6, wherein the semi-permeable layer is arranged between the layer of matrix material and the one of the impermeable layers having the at least one opening.

10. The test device according to claim 6, wherein said at least one opening comprises a plurality of openings.

11. The test device according to claim 1, wherein the reagent is capable of acting as an assay for at least one chemical or biological analyte in a sample.

12. The test device according to claim 11, wherein the analyte is a protein, carbohydrate, sugar, ligand or anti-ligand.

13. The test device according to claim 1, wherein the reagent is a ligand or anti-ligand.

14. The test device according to claim 1, wherein the reagent is capable of detecting the pH of a sample.

15. The test device according to claim 1, the matrix material further carrying any one or more of: a culture medium, a gel, a conductive material or a thin film battery.

16. The test device according to claim 1 being suitable for clinical or hygiene testing.

17. The test device according to claim 1, wherein the matrix material carries the reagent supported on particles.

18. The test device according to claim 6, wherein the reagent is capable of acting as an assay for at least one chemical or biological analyte in a sample.

19. The test device according to claim 18, wherein the analyte is a protein, carbohydrate, sugar, ligand or anti-ligand.

20. The test device according to claim 6, wherein the reagent is a ligand or anti-ligand.

21. The test device according to claim 6, wherein the reagent is capable of detecting the pH of a sample.

22. The test device according to claim 6, the matrix material further carrying any one or more of: a culture medium, a gel, a conductive material or a thin film battery.

23. The test device according to claim 6 being suitable for clinical or hygiene testing.

24. The test device according to claim 6, wherein the matrix material carries the reagent supported on particles.

25. The test device according to claim 1, comprising a means for increasing the concentration of the sample applied to the matrix material at a site where the reagent is carried.

26. The test device according to claim 1, wherein the impermeable layer having the plurality of openings further defines a contact surface for wiping over the surface that facilitates detachment of the sample from the surface.

27. The test device according to claim 1, wherein each opening of the plurality is locally separated from the other openings of the plurality and aligned with the patterned surface of the matrix material to increase the intensity of a color reaction by making a color change more visible.

28. The test device according to claim 1, wherein the patterned surface of the matrix material comprises a surface pattern applied by a printing technique.

29. The test device according to claim 28, wherein the patterned surface of the matrix material comprises a relief patterned by the printing technique.

30. The test device according to claim 29, wherein the relief on the patterned surface comprises an embossed array of grooves, grids and/or circles.

31. The test device according to claim 1, wherein the sample contacts the matrix material at a location corresponding to an opening of the plurality of openings, wherein the plurality of openings on the impermeable layer and/or the matrix material are configured to increase a concentration of the sample at the location on the matrix material for reaction with the reagent.

32. The test device according to claim 31, wherein the plurality of openings of one of the impermeable layers and/or the matrix material are configured to locally saturate the matrix material with the sample at the location to form a local concentration barrier that enhances detectability of a reaction of the sample with the reagent.

33. The test device according to claim 31, wherein the opening defines a peripheral boundary and a local concentration barrier of the sample is defined on the matrix material corresponding to the peripheral boundary.

34. The test device according to claim 31, wherein the matrix material has a relief pattern.

35. The test device according to claim 34, wherein the relief pattern comprises an embossed array of grooves, grids and/or circles.

36. The test device according to claim 34, wherein the relief pattern is printed on the matrix material.

37. The test device according to claim 31, wherein the matrix material has a surface with an impermeable region patterned thereon.

38. The test device according to claim 1, wherein the plurality of openings in the impermeable layer facilitates transfer of the sample from the surface to the matrix material within the test device.

39. The test device according to claim 38, wherein the impermeable layer having the plurality of openings through which the sample may be absorbed comprises a patterned surface to promote detachment of the sample from the surface.

40. The test device according to claim 39, wherein the patterned surface comprises a feature selected from the group consisting of: grooves, nodules, and combinations thereof.

41. The test device according to claim 39, wherein the patterned surface is embossed or imprinted.

42. The test device according to claim 6, comprising a means for increasing the concentration of the sample applied to the matrix material at a site where the reagent is carried.

43. The test device according to claim 6, comprising a means for assisting detachment of the sample from the surface.

44. The test device according to claim 6, comprising a means for increasing the intensity of a color reaction by making a color change more visible.

45. The test device according to claim 6, wherein the matrix material comprises a surface pattern applied by a printing technique.

46. The test device according to claim 45, wherein the matrix material comprises a surface defining a relief patterned by the printing technique.

47. The test device according to claim 46, wherein the relief comprises an embossed array of grooves, grids and/or circles.

48. The test device according to claim 6, wherein the sample contacts the matrix material at a location corresponding to an opening of the at least one opening, wherein the at least one opening on the impermeable layer and/or the matrix material is configured to increase a concentration of the sample at the location on the matrix material for reaction with the reagent.

49. The test device according to claim 48, wherein the at least one opening of one of the impermeable layers and/or the matrix material is configured to locally saturate the matrix material with the sample at the location to form a local concentration barrier that enhances detectability of a reaction of the sample with the reagent.

50. The test device according to claim 48, wherein the opening defines a peripheral boundary and a local concentration barrier of the sample is defined on the matrix material corresponding to the peripheral boundary.

51. The test device according to claim 48, wherein the reagent reacts with the sample to exhibit a detectable color change and the increased concentration of the sample in the matrix material increases intensity of any detectable color change as compared to a test device lacking the at least one opening in one or more of the impermeable layers.

52. The test device according to claim 48, wherein the matrix material has a relief pattern.

53. The test device according to claim 52, wherein the relief pattern comprises an embossed array of grooves, grids and/or circles.

54. The test device according to claim 52, wherein the relief pattern is printed on the matrix material.

55. The test device according to claim 48, wherein the matrix material has a surface with an impermeable region patterned thereon.

56. The test device according to claim 6, wherein the at least one opening in the impermeable layer facilitates transfer of the sample from the surface to the matrix material within the test device.

57. The test device according to claim 56, wherein the impermeable layer having the at least one opening through which the sample may be absorbed comprises a patterned surface to promote detachment of the sample from the surface.

58. The test device according to claim 57, wherein the patterned surface comprises a feature selected from the group consisting of: grooves, nodules, and combinations thereof.

59. The test device according to claim 57, wherein the patterned surface is embossed or imprinted.

60. The test device according to claim 1, wherein at least a portion of at least one impermeable layer is transparent.

61. The test device according to claim 6, wherein at least a portion of at least one impermeable layer is transparent.

62. A test device for wiping over a surface to extract a sample, the test device comprising:

two flexible impermeable layers;

a flexible layer of absorbent matrix material arranged between the flexible impermeable layers, the matrix material having a reagent applied thereto and having a patterned surface, one of the flexible impermeable layers having at least one opening aligned with the flexible absorbent matrix material and through which the sample may be absorbed into the flexible absorbent matrix material as facilitated by the wiping over the surface; and a one-way flow flexible semi-permeable layer extending across the at least one opening and located immediately adjacent the flexible absorbent matrix material and between the two flexible impermeable layers, the one-way flow flexible semi-permeable layer being made of a semi-permeable material which only allows the sample to pass in a direction towards the flexible absorbent matrix material, but limits backflow of the reagent from the flexible absorbent matrix material, wherein the patterned surface of the flexible absorbent matrix material reduces spreading and increases a concentration of the sample in regions of the flexible absorbent matrix material corresponding to the at least one opening.

63. The test device according to claim 1, wherein each respective opening of the plurality of openings comprises an edge that facilitates extraction of the sample from the surface during the wiping.

64. The test device according to claim 26, wherein the contact surface of the impermeable layer having the plurality of openings further comprises embossed grooves, nodules, or embossed patterns to improve detachment of the sample from the surface.

65. A test device for wiping over a surface to extract a sample, the test device comprising:

two impermeable layers; and a layer of absorbent matrix material arranged between the impermeable layers and located immediately adjacent both impermeable layers, the matrix material carrying a reagent, a culture medium, and either a conductive material or a thin film battery for heating or warming the culture medium, and one of the impermeable layers having a plurality of openings aligned with the matrix material and through which the sample may be absorbed into the matrix material as facilitated by the wiping over the surface.

66. A test device for wiping over a surface to extract a sample, the test device comprising:

two impermeable layers;

a layer of absorbent matrix material arranged between the impermeable layers and located immediately adjacent a first of the two impermeable layers, the matrix material having a reagent applied thereto and carrying a culture medium and either a conductive material or a thin film battery for heating or warming the culture medium, one of the impermeable layers having at least one opening aligned with the matrix material and through which the sample may be absorbed into the matrix material as facilitated by the wiping over the surface; and a semi-permeable layer extending across the at least one opening and located immediately adjacent the absorbent matrix material and a second of the two impermeable layers, the semi-permeable layer being made of a semi-permeable material which allows the sample to pass therethrough whilst limiting backflow of the reagent from the matrix material.

* * * * *

UNITED STATES PATENT AND TRADEMARK OFFICE

CERTIFICATE OF CORRECTION

PATENT NO. : 8,697,006 B2
APPLICATION NO. : 11/920578
DATED : April 15, 2014
INVENTOR(S) : Häivä et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this
Twenty-ninth Day of September, 2015

Michelle K. Lee

Michelle K. Lee
*Director of the United States Patent and Trademark Office*